(12) United States Patent
Gardner

(10) Patent No.: US 6,610,274 B1
(45) Date of Patent: Aug. 26, 2003

(54) ANTI-INFLAMMATORY COMPOSITION COMPRISING TETRACYCLINE

(76) Inventor: Wallace J. Gardner, 1791 Mass Ave., Cambridge, MA (US) 02140

( * ) Notice: Subject to any disclaimer, the term of this patent is extended or adjusted under 35 U.S.C. 154(b) by 0 days.

(21) Appl. No.: 10/023,017

(22) Filed: Dec. 18, 2001

Related U.S. Application Data

(60) Provisional application No. 60/258,027, filed on Dec. 22, 2000.

(51) Int. Cl.$^7$ ............................ A61K 7/16; A61K 31/65
(52) U.S. Cl. ........................................ 424/49; 514/152
(58) Field of Search ...................... 514/152; 424/49–58

(56) References Cited

U.S. PATENT DOCUMENTS

| | | | | |
|---|---|---|---|---|
| 2,730,483 A | * | 1/1956 | Mast ............................ 167/65 |
| 3,029,191 A | * | 4/1962 | King ............................ 167/93 |
| 3,152,181 A | * | 10/1964 | Shapiro et al. .............. 260/564 |
| 3,155,580 A | * | 11/1964 | Bergy et al. .................. 167/65 |
| 3,160,565 A | * | 12/1964 | Dveil ........................... 167/82 |
| 3,183,230 A | * | 5/1965 | Shapiro et al. .............. 260/244 |
| 3,227,617 A | * | 1/1966 | Manahan et al. ............. 167/93 |
| 3,227,618 A | * | 1/1966 | Manahan et al. ............. 167/93 |
| 3,268,404 A | * | 8/1966 | Banford et al. ............. 167/53.1 |
| 3,299,124 A | * | 1/1967 | Boissier et al. ............. 260/501 |
| 3,312,594 A | * | 4/1967 | Cyr et al. ..................... 167/82 |
| 3,344,022 A | * | 9/1967 | Johnston ................... 167/53.1 |
| 3,380,885 A | * | 4/1968 | Miller ....................... 167/53.1 |
| 3,459,854 A | * | 8/1969 | Boissier et al. ............. 426/128 |
| 3,525,791 A | * | 8/1970 | Ahrens ....................... 424/280 |
| 3,527,864 A | * | 9/1970 | MacMillan et al. ......... 424/177 |
| 3,651,208 A | * | 3/1972 | Laustier ....................... 424/54 |
| 3,839,566 A | * | 10/1974 | MacMillan et al. ......... 424/243 |
| 4,780,320 A | * | 10/1988 | Baker .......................... 424/493 |
| 4,919,939 A | * | 4/1990 | Baker .......................... 424/493 |
| 5,082,653 A | * | 1/1992 | Pan et al. ..................... 424/54 |
| 5,110,720 A | | 5/1992 | Csanyi et al. ................ 433/215 |
| RE34,656 E | | 7/1994 | Golub et al. ................. 514/152 |
| 5,330,357 A | * | 7/1994 | Keller ......................... 433/215 |
| 5,366,733 A | * | 11/1994 | Brizzolara et al. .......... 424/426 |
| 5,622,498 A | * | 4/1997 | Brizzolara et al. ............ 433/80 |
| 5,770,588 A | | 6/1998 | McNamara et al. ......... 514/152 |
| 5,855,904 A | * | 1/1999 | Chung et al. ............... 424/426 |
| 5,891,422 A | * | 4/1999 | Pan et al. ...................... 424/49 |
| 6,193,994 B1 | * | 2/2001 | Lee et al. .................... 424/444 |
| 6,348,187 B1 | * | 2/2002 | Pan et al. ...................... 424/53 |

OTHER PUBLICATIONS

Abstract of Firatel et al J. Clin. Period. 200. 21(10); 680–683, Nov. 1994.*
Ms. Flossy's Dental Hygiene News—Dental Info Publication 4–Pages. Jun. 24, 2002.

\* cited by examiner

*Primary Examiner*—Shep K. Rose
(74) *Attorney, Agent, or Firm*—Nields & Lemack

(57) ABSTRACT

Therapeutic composition having anti-infective activity. The therapeutic composition is a formulation comprising an antibiotic, preferably a tetracycline, most preferably doxycycline, which has not been chemically modified to eliminate antimicrobial efficacy. The antibiotic is preferably in a liquid vehicle, most preferably one that contains at least 20% alcohol by volume. The therapeutic composition is preferably in local delivery form and is self-administered orally or via the nasal cavity. Administration of the therapeutic composition of the present invention treats diseases that originate from the oral cavity or that do not originate in the oral cavity, but are affected by contaminants, such as viruses or bacteria, in the oral cavity entering the bloodstream including but not limited to periodontal disease, sinusitis, gingivitis, the common cold, sore throat, influenza, allergies (particularly to tree pollen), resistant pneumonia, diseases of the gastrointestinal tract, inflammatory diseases such as rheumatoid arthritis, cancer, ulcers, heart disease, etc.

1 Claim, No Drawings

ANTI-INFLAMMATORY COMPOSITION COMPRISING TETRACYCLINE

This application claims the benefit of Provisional Application No. 60/285,027 filed Dec. 22, 2000.

BACKGROUND OF THE INVENTION

The accumulation bacteria in the oral cavity, such as on the teeth or tongue has been identified as a contributor or cause of various inflammatory conditions, including gingivitis, periodontitis and other gum diseases. Treatment of the oral cavity with antibiotics to reduce or eliminate the effects of bacteria is known. For example, broad spectrum antibiotics such as tetracyclines and metronidazole have been used in the treatment of periodontal disease to reduce oral cavity microflora. Typically such use has been systemic, which can result in various undesirable side effects, including the threat or danger or building allergies or immunity to the antibiotic, overgrowth of opportunistic yeast and fungi and intestinal disturbances.

Many other common inflammatory diseases, such as sinusitis, diseases of the gastrointestinal tract (including those that manifest themselves in stomach and bowel problems), the common cold, influenza, allergies, halitosis, pneumonia, etc., also may be caused by viruses and/or bacteria. Often the source of the bacteria and viruses is the oral cavity, especially the ear, nose and throat passages, and the sinuses. Once the bacteria and/or viruses are resident in the oral cavities or sinuses (e.g., the maxillary, frontal and ethmoid), they can continually cause infection through circulation in the blood stream. Continual reduction or elimination of these bacteria and viruses would reduce chronic infection in the body.

SUMMARY OF THE INVENTION

The problems of the prior art have been overcome by the present invention, which provides a therapeutic composition having anti-infective activity. In a preferred embodiment, the therapeutic composition is a formulation comprising an antibiotic, preferably a tetracycline, most preferably doxycycline, which has not been chemically modified to eliminate antimicrobial efficacy. The antibiotic is preferably in a liquid vehicle, most preferably one that contains at least 20% alcohol by volume. The therapeutic composition is preferably in local delivery form and is preferably self-administered orally or via-the nasal cavity. The therapeutic composition most preferably is a self-delivered formulation in local delivery form that consists essentially of a tetracycline, most preferably doxycline, which has not been chemically modified to eliminate antimicrobial efficacy, and a liquid vehicle, more preferably one which contains at least 20% alcohol by volume, and most preferably one which consists essentially of sterile water or Listerine or the like, which tetracyline is preferably present in the formulation in the amount of between 50 to 100 mgs per ounce of liquid vehicle.

Administration of the therapeutic composition of the present invention treats diseases that originate from the oral cavity or that do not originate in the oral cavity, but are affected by contaminants, such as viruses or bacteria, in the oral cavity entering the bloodstream including but not limited to periodontal disease, sinusitis, gingivitis, the common cold, sore throat, influenza, allergies (particularly to tree pollen), resistant pneumonia, diseases of the gastrointestinal tract, inflammatory diseases such as rheumatoid arthritis, cancer, ulcers, heart disease, etc.

DETAILED DESCRIPTION OF THE INVENTION

The therapeutic compositions of the present invention are local delivery compositions that have anti-infective activity and comprise an antibiotic, preferably a tetracycline which has not been chemically modified to eliminate antimicrobial efficacy. The compositions are effective to prevent pollutants from passing from oral passages into the blood stream.

The tetracyclines useful in the compositions of the present invention include apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin, and tetracycline. Doxycycline is particularly preferred.

The therapeutic composition of the invention also includes a carrier which is any compatible, nontoxic substance suitable to deliver the antibiotic. Carriers can include sterile water, alcohol, fats, waxes, inert solids and even liposomes. Preferably, the antibiotic is in a liquid vehicle. Water is a preferred liquid for the liquid vehicle and the vehicle even more preferably comprises at least about 20% alcohol by volume, more preferably 20–40% alcohol and most preferably about 20–28% alcohol. Preferably, the therapeutic composition does not include a morpholinoamino alcohol or pharmaceutically-acceptable salt thereof. One particularly preferred formulation includes a mixture of doxycline with Listerine®, which is 0.064% thymol, 0.092% eucalyptol, 0.060% methylsalicylate, 0.042% menthol, 26.9% alcohol, poloxamer 407, water, sodium benzoate and caramel. Other suitable formulations include a mixture of doxycline with other commercially available mouthwashes, oral rinses or anti-plaque formulations. Pharmaceutically acceptable adjuvants may also be incorporated into the therapeutic composition. In certain therapeutic compositions of the invention, antiphlogisitic agents are not preferred. The compositions of the present invention also may contain various inactive ingredients, such as sweeteners (natural and artificial), flavorings (natural or artificial), colorants, preservatives, etc.

The amount of antibiotic used in the formulation depends upon the frequency of the dose, the particular infection and the severity of the infection being treated, the method of local administration of the composition and the effect desired (including whether the treatment is a prophylactic or therapeutic application). Actual methods for preparing administrable compositions will be known or apparent to those skilled in the art and are described in more detail in, for example, Remington's Pharmaceutical Science, $17^{th}$ Ed., Mack Publishing Co., Easton, Pa. (1985), which is incorporated herein by reference. Preferably the formulation contains from about 50 to about 100 mgs tetracycline, preferably doxycline, per ounce of total liquid in the formulation. The formulation is prepared by mixing the tetracycline with the liquid vehicle and shaking the mixture.

Alternative forms of the therapeutic composition of the present invention include lozenges, chewing gum, toothpaste, salve, ointments and gels. The compositions also can be provided in the form of a kit, including the tetracycline and the liquid vehicle.

In the preferred form of the present invention, the therapeutic composition is a mouthwash or a rinse, nose drops or ear drops, and is self-administered. For example, the mouthwash or rinse can be introduced into the mouth and held in the mouth for at least 30 seconds and preferably at least 1 minute. During the holding period, the mouthwash or rinse is preferably swirled around the mouth in order to bathe the teeth and gums in the composition. Gargling with the mouthwash and rinse during this holding period can also be carried out. The mouthwash or rinse is then expelled from the mouth into a waste receptacle. This procedure can be carried out at least once daily, preferably 2–6 times daily. If the mouthwash or rinse is being given for preventative purposes, then the rinse is preferably used twice a day, preferably in the AM and in the PM on a long-term basis and preferably consists of 50 mgs of antibiotic, preferably doxycline per 1 ounce of liquid vehicle. The rinse can be used continually for many years without diminishing its benefits, and with no adverse side effects. The rinse can be use on an acute basis or for continual periods as long as 3 months, 6 months, 1 year, 2 years, 5 years or greater. Long term use of more than 5 years with no reported adverse side effects is documented. If the mouthwash or rinse is being used to treat an acute infection, the dosage of antibiotic, preferably doxycline, is doubled to 100 mgs per ounce of liquid vehicle and the rinse is preferably used between 4 to 6 times a day during the period of acute infection. Nosedrops are particularly useful for treating or preventing sinusitis. If nosedrops comprising the therapeutic composition of the invention are used, between 3 to 10, preferably 4 to 7, and more preferably 5 drops should be placed in each nostril between 3 to 5 times per day, based on the severity of the infection. This should be done for approximately one week. Administration of the composition of the present invention to the oral cavity cleanses the oral cavity of bacteria and/or viruses, and reduces or eliminates inflammation and concomitant diseases and conditions associated therewith. Additionally, reduction or elimination of bacteria and/or viruses in the oral cavity reduces the concentration of bacteria and/or viruses that are absorbed into the bloodstream, and therefore reduces their effect throughout the body.

Without intending to be bound to any mechanism of action, it is believed that cleansing the oral cavity with a therapeutic composition of the invention prevents the blood from being contaminated and therefore prevents and aids in treating diseases such as heart disease, cancer and ulcers caused in part or in whole by toxins or contaminants which have entered the bloodstream through the oral cavity and have attached themselves to the walls of small blood vessels in the heart, pancreas, breast, stomach, bowel, etc. and serve as irritants to cause ulcers, intestinal irritations, and growths and plaque in blood vessels.

The terms "treatment" or "treating" or "treat(s)" as used herein in reference to diseases include 1) preventing such diseases from occurring in a subject who may be predisposed to such disease or diseases but who has not yet been diagnosed as having it or them; 2) inhibiting these diseases, i.e. arresting their development; or 3) ameliorating or relieving the symptoms of these diseases, i.e., causing regression of the disease state. "Therapeutic" as used herein includes compositions for prophylactic treatment of diseases.

The amount of antibiotic, e.g. doxycycline, used in the therapeutic compositions and the dosage selection is an amount and dosage effective to achieve anti-infective activity, i.e. the amount necessary to effectively treat the infection. Dosage regimens will depend on the dosage and effectiveness thereof, the intended use, the route of administration, the severity of the disease, the body weight of the mammal or human being treated and the patient's general state of health. Although suitable amounts of antibiotic in-the therapeutic composition are within the range of 50 to 100 mg per ounce of liquid vehicle, those skilled in the art will determine optimum concentrations and dosages from clinical experience in order to carry out the method of the invention. For example, the physician or dentist treating the patient may begin the patient on a normal strength mouth rinse of 50 mg per ounce of liquid vehicle and then increase the strength of the dose and potentially add nose drops where indicated. Blood cultures and growth cultures can be done after the rinse is used in order to define the optimum dosage more precisely. The amount of therapeutic composition used to treat the patient is defined herein as a therapeutically effective dose.

EXAMPLE 1

A 100 mg and a 50 mg capsule of doxycycline were opened and the contents added to 3 ounces of Listerine® mouthwash. This mixture was shaken until the doxycycline was dispersed in the mouthwash.

A patient with gum infection administered one ounce of the mixture into the mouth and swirled in the mouth for 30 seconds, three times daily for three months. The upper molar gum infection healed within several days. Gumline recession ceased. Stools normalized and sinuses cleared, despite a history of chronic sinusitis. Taste bud sensitivity was enhanced.

What is claimed is:

1. A method of treating a mammal suffering from chronic sinusitis disease, comprising administering to said mammal an effective amount of a therapeutic composition consisting essentially of a tetracycline which has not been chemically modified to eliminate antimicrobial efficacy and a liquid mouthwash vehicle comprising at least 20% alcohol by volume, with the proviso that said therapeutic composition is devoid of amorpholinoamino alcohol or pharmaceutically acceptable salt thereof.

* * * * *